United States Patent [19]
Haber et al.

[11] Patent Number: 5,114,411
[45] Date of Patent: May 19, 1992

[54] MULTI-CHAMBER VIAL

[75] Inventors: Terry M. Haber, Lake Forest; Clark B. Foster, Laguna Niguel; William H. Smedley, Lake Elsinore, all of Calif.

[73] Assignee: Habley Medical Technology Corporation, Laguna Hills, Calif.

[21] Appl. No.: 615,610

[22] Filed: Nov. 19, 1990

[51] Int. Cl.$^5$ .................. A61M 5/24; A61M 37/00
[52] U.S. Cl. ...................... 604/203; 604/87
[58] Field of Search ............... 604/191, 201, 203, 204, 604/239, 411-416, 82, 87, 86, 88, 89, 90, 91

[56] References Cited

U.S. PATENT DOCUMENTS

| Re. 29,656 | 6/1978 | Chittenden et al. | 604/413 |
|---|---|---|---|
| 2,665,690 | 1/1954 | Lockhart | 604/416 |
| 3,314,563 | 4/1967 | Mounier | 604/416 |
| 3,563,415 | 2/1971 | Ogle | 604/90 |
| 3,696,919 | 10/1972 | Miles | 604/416 |
| 3,809,225 | 5/1974 | Allet-Coche | 604/90 |
| 3,856,138 | 12/1974 | Maekawa | 604/416 |
| 3,923,059 | 12/1975 | Ogle | 604/414 |
| 4,031,892 | 6/1977 | Hurschman | 604/88 |
| 4,059,112 | 11/1977 | Tischlinger | 604/413 |
| 4,529,403 | 7/1985 | Kamstra | 604/191 |
| 4,589,879 | 5/1986 | Pearson | 604/88 |
| 4,624,667 | 11/1986 | Rutnarak | 604/88 |
| 4,713,062 | 12/1987 | Stevanato | 604/203 |
| 4,781,679 | 11/1988 | Larkin | 604/416 |
| 4,969,883 | 11/1990 | Gilbert | 604/414 |

FOREIGN PATENT DOCUMENTS 0407559 3/1934 United Kingdom ............... 604/416

OTHER PUBLICATIONS

Product literature for Mix-O-Vial of the Upjohn Company.
Advertising flyer for the ADD-Vantage ® System of Abbot Laboratories, Mar. 1990.
Packaging, "Packaging Breakthrough Yields Savings for Hospitals," Feb. 1986.
Advertising flyer entitled "Kendall McGaw Introduces EXCEL ®".
ADD-Vantage ® wall chart, Abbott Laboratories, Dec., 1989.
Photocopy of conventional IV bag made by Travenol Laboratories, Deerfield, Ill.

Primary Examiner—C. Fred Rosenbaum
Assistant Examiner—Sharon Finkel
Attorney, Agent, or Firm—Townsend and Townsend

[57] ABSTRACT

A vial (2) has first and second chambers (56, 54) initially separated by a rupturable barrier (20). The first chamber is a variable volume chamber defined by a cylinder (18), the rupturable barrier at the second end (19) of the cylinder and a piston (14). The second chamber is created by a telescoping container (22) mounted to a second end of the cylinder. The chambers are telescopically collapsed causing fluid pressure in the second chamber to rupture the barrier so the components mix in the first chamber. The piston is driven through the cylinder from pre-mix to post-mix positions by the liquid from the second chamber. This dislodges a safety shield at the first end of the cylinder to expose the piston. The mixed contents of the first, variable volume chamber are removed by inserting a needle cannula through the now exposed piston; aspiration of the mixed contents take place without the introduction of air into the first chamber since the piston moves back down the cylinder as the contents are removed. A spike adapter can be used to transfer the contents of the vial to a conventional IV bag.

8 Claims, 8 Drawing Sheets

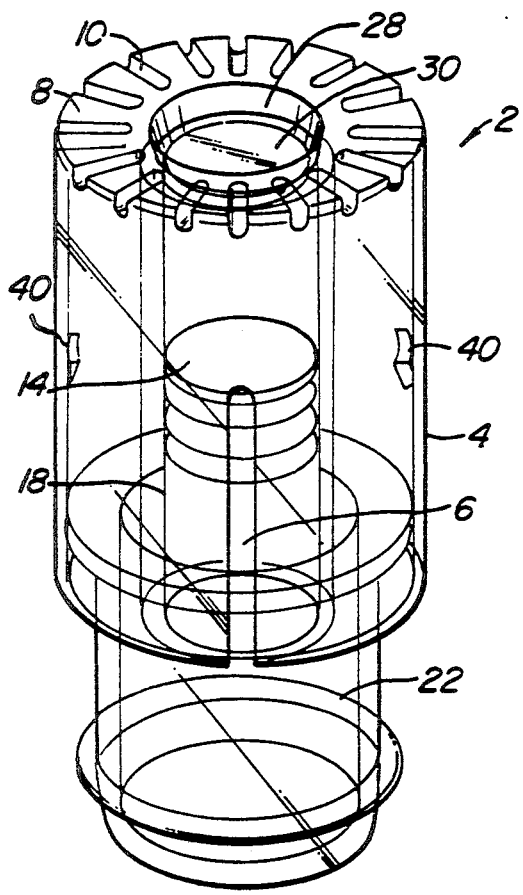
FIG. 1.
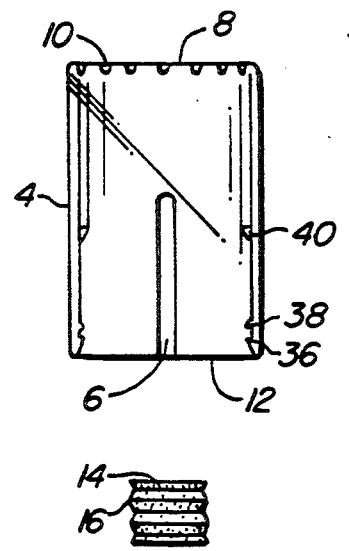
FIG. 2.
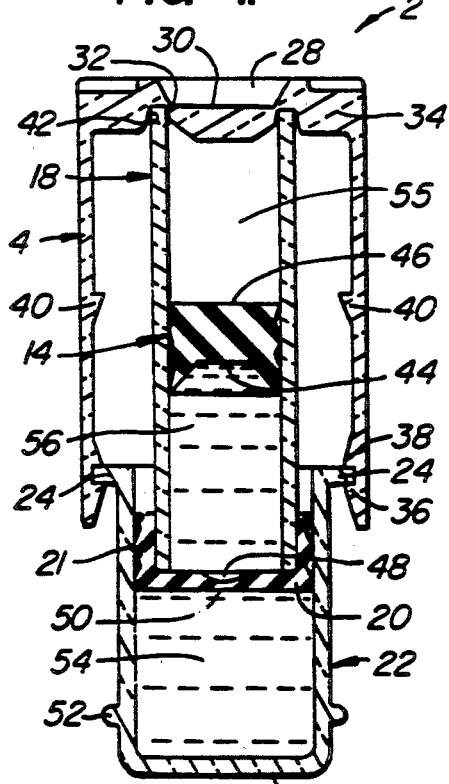
FIG. 3.
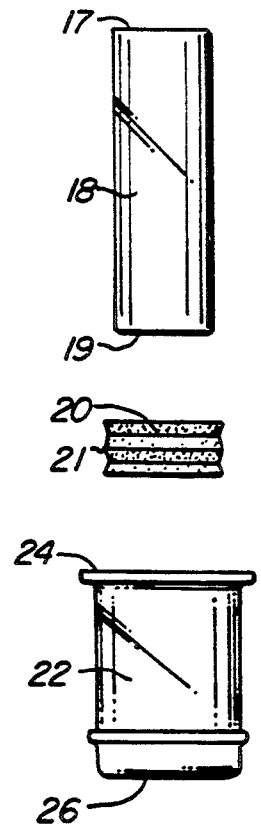

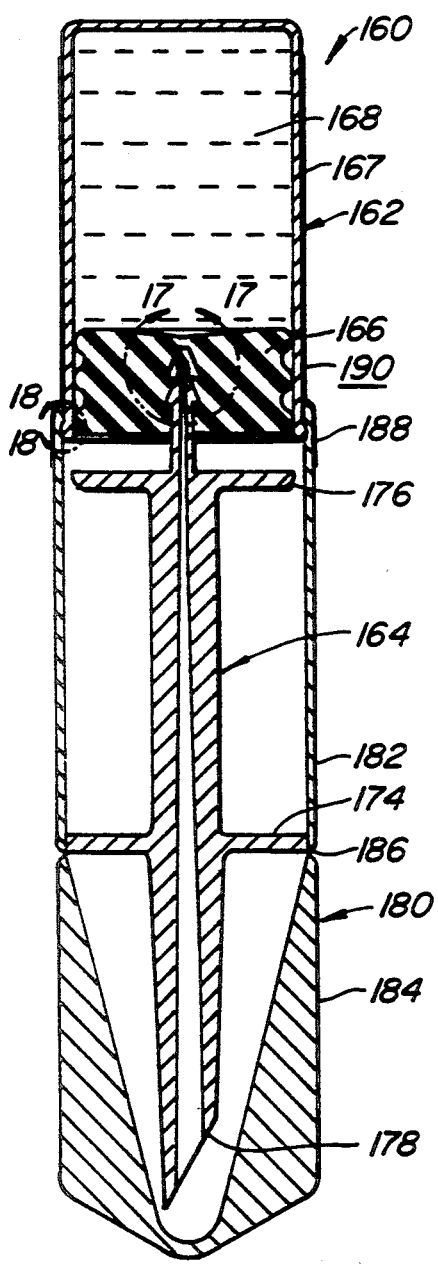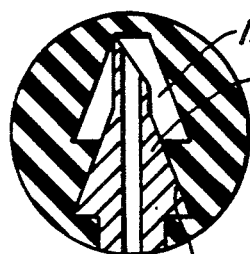
FIG. 17.
FIG. 18.
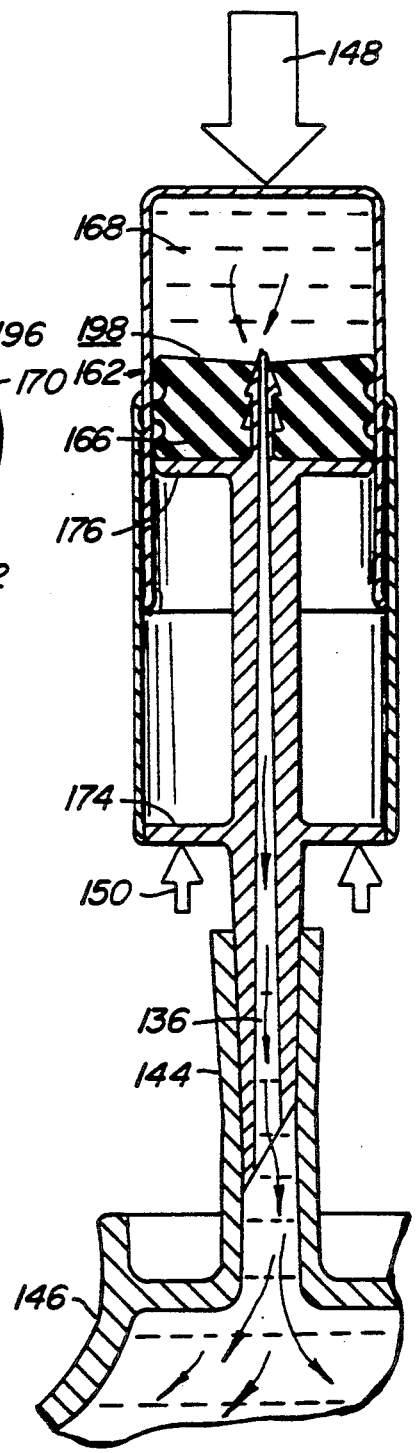
FIG. 16.
FIG. 19.

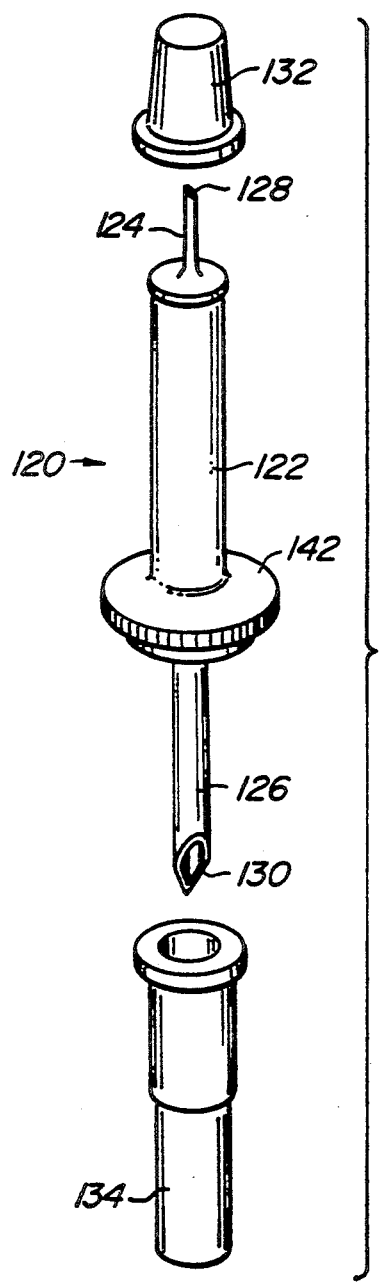
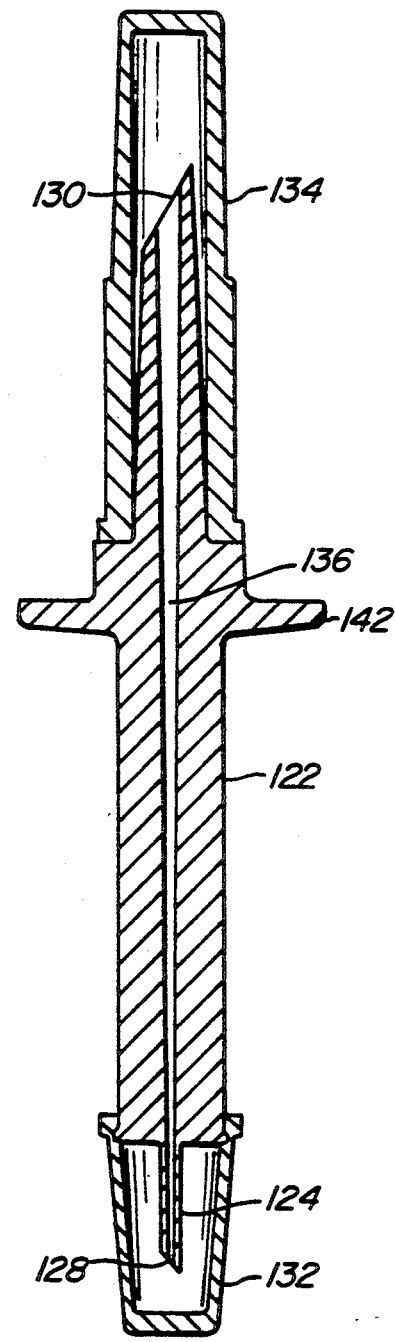
FIG. 10.
FIG. 11.

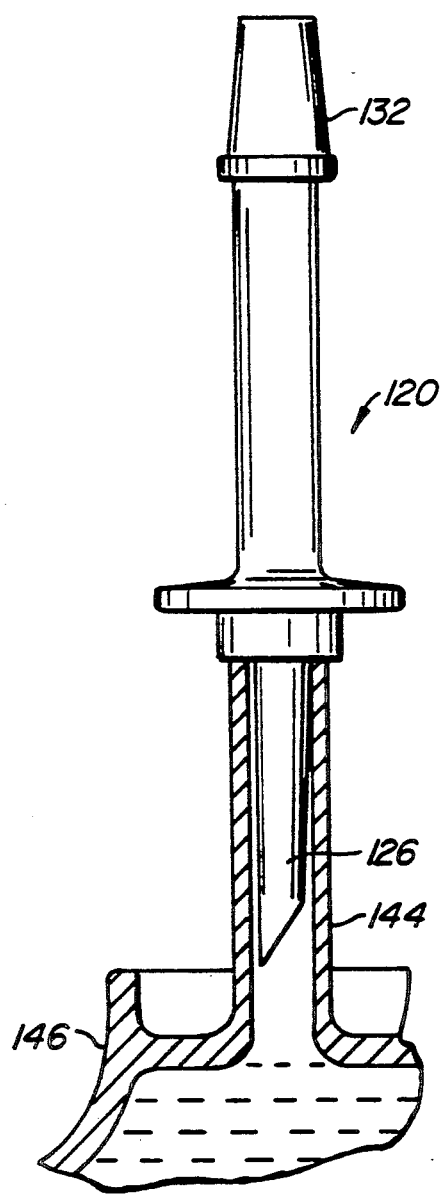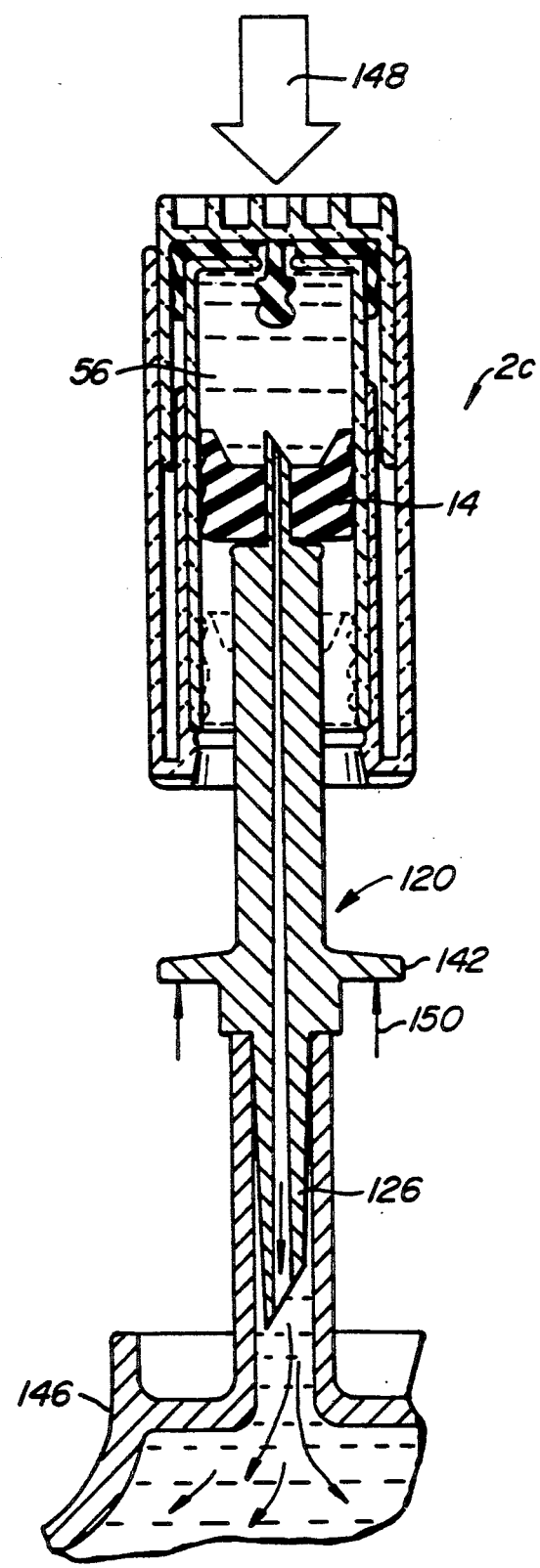
FIG. 12.
FIG. 13.

MULTI-CHAMBER VIAL

BACKGROUND OF THE INVENTION

Safe and effective drug therapy by injection depends not only upon accurate diagnosis, but also on efficient and reliable introduction of the medical substance into the subcutaneous cellular tissue without introducing contaminants or ambient air. The applicable drug or pharmaceutical must first be drawn from the resident container or vial into a syringe before injection. The integrity and features of the vial, therefore, are influential over the overall safety of the injection.

Typically, great care must be taken when a needle cannula of a syringe is used in conjunction with a vial containing a pharmaceutical to be administered to the patient As the pharmaceutical is drawn out of the container via the needle cannula, precautions must be taken to avoid air being drawn into the syringe In rigid vials, air must be introduced into the container to fill the void created as the liquid pharmaceutical is withdrawn. This volume of air then becomes susceptible to being mixed with the pharmaceutical or being drawn in through the needle cannula and creating air pockets in the syringe barrel. Catastrophic consequences could result if these air pockets are subsequently injected into the patient along with the liquid pharmaceutical.

Some medical conditions necessitate such a rapid diagnosis and administration of the necessary injection that precautionary measures needed to eliminate air content in the syringe are often compromised. As an example, diagnosis and treatment of acute myocardial infarction requires rapid injection of a thrombolytic agent adjacent to the atherosclerotic plaque in a major epicardial coronary vessel Minutes, or even seconds, can have profound impact on the treatment of the patient Thrombolytic agents, such as tissue plasminogen activator (TPA) or streptokinase usually must be injected immediately, while taking the time for necessary precautions needed to prohibit air from becoming entrapped and compromising the drug.

Problems associated with injections are further complicated when the medication to be administered must be stored as two separate component parts, then mixed, prior to injection. Dual chamber vials have been developed to facilitate storage and mixing of these two-component medications. Common examples of multipart medications include medications which must be mixed from a component A, usually a preservative or catalyst, and a component B, which is usually a pharmaceutical. Component A or component B may be in powder or crystalline form instead of liquid form.

Recently, dual chamber vials have been developed which allow an A component and a B component to remain separated in independent chambers within a single package until mixing is desired. The vial allows mixing of the component parts in that same unitary package. In an example of such a device is the MIX-0-VIAL two compartment vial manufactured by the Upjohn Company of Kalamazoo, Michigan. This device is a single vial container having two chambers separated by a small stopper. The septum is formed by a plunger-stopper at one end which is used to pressurize the contents of one chamber so to displace a plug lodged in a small orifice separating the two chambers. As the plunger stopper is displaced (by giving it a quarter turn), the plug floats freely into one of the chambers and is used as an agitator to mix the two component parts together. The two components are free to flow between chambers through the connecting orifice and thereby mix together. Although this device is a significant advance in dual chamber vials, the device has least two significant disadvantages. First, once the protective cap is removed, there is nothing to prohibit a user from penetrating the septum with a needle cannula and inadvertently drawing out only one of the component parts separately prior to mixing. Such an event could be extremely hazardous to the health of the patient. Second, even when the two components are properly mixed, when a needle cannula penetrates the septum and draws out the mixed medication, air becomes entrapped in the vial as air enters to replace the removed liquid as the medication is withdrawn. Time consuming precautions must be taken to carefully avoid entrapping air in the syringe and injecting the same into the patient.

SUMMARY OF THE INVENTION

The present invention is directed to a multi-chamber vial which provides both protection against inadvertent withdrawal of one of the component parts of the multipart medication prior to mixing, and a mechanism which eliminates entrapment of air in the medication chamber as the medication is withdrawn.

Generally, the invention relates to vials used for containment of medication substances or pharmaceuticals. More specifically, the invention relates to vial which can store pharmaceuticals made from two component parts where there is a desire to keep the two component parts separated until the time necessary to mix the components together. The device has two (or more) chambers separated by a rupturable barrier which keeps the component parts isolated from each other until mixing is desired. The device is made from materials which eliminate the possibility of a needle cannula piercing the septum to access either component of the pharmaceutical prior to mixing.

When the components are to be mixed, the contents of one chamber are forced into the other chamber by pressurizing the contents of the one chamber. This is preferably accomplished using a telescoping device so the opposite ends of the device are simply pressed together causing fluid pressure to rupture the barrier separating the two chambers. The one chamber could also be in the form of a flexible bag, a bellows or such other structure. The rupturing can be by dislodging a plug or like element, tearing a flexible diaphragm, breaking a solid frangible sealing element, moving a resilient sealing element, or by other means. Once the barrier is ruptured, the component in the one chamber, typically the lower chamber, is forced into the upper chamber as the device is compressed. The two components are mixed by the resulting turbulence as the upper chamber fills with the mixed pharmaceutical.

The upper chamber is a variable volume chamber. This is achieved by making the upper chamber a piston and tube, preferably a cylinder, arrangement. The piston travels within the cylinder to increase the size of the upper chamber as the fluid volume grows. The piston continues to travel until both components are within the upper chamber; at this point, the piston is forced against a removable safety shield covering the upper end of the cylinder. Only when the safety shield is dislodged from its position covering the end of the cylinder is the user permitted access to the contents of the vial through the piston.

The piston serves several functions: it permits the upper chamber to be a variable volume chamber to permit mixing of two liquid components without the entrainment of air; it serves as the septum to permit user access to the mixed contents of the upper chamber by a hollow needle; it permits the upper chamber to automatically lessen its volume as the mixed contents are removed to eliminate the need to introduce air into the chamber and thus reduce risk; it acts to automatically dislodge the safety shield once the contents of the chambers are combined. When mixing a solid and a liquid, the solid being in the upper chamber, the use of the piston minimizes the amount of air or other gas in the upper chamber.

Other features and advantages of the invention will appear from the following description in which the preferred embodiment has been set forth in detail in conjunction with the accompanying drawings.

BRIEF DESCRIPTION OF THE DRAWINGS

FIG. 1 is a perspective view of a preferred embodiment of the invention fabricated primarily from clear materials and showing the vial in the inactivated or premixed condition.

FIG. 2 is an exploded side view of the device shown in FIG. 1 illustrating the various component parts.

FIG. 3 is a cross-sectional view of the dual chamber vial in the inactivated condition of FIG. 1 showing a first and second chamber separated by a diaphragm.

FIG. 10 is a perspective view of a spike adapter used to connect the vial of FIG. 1 with a conventional IV bag.

FIG. 11 is a cross-sectional side view of the spike adapter shown in FIG. 10.

FIG. 12 is a partial cross section side view of the spike adapter shown in FIG. 10 connected to a spike port of a conventional IV bag.

FIG. 13 is a cross section view of the spike adapter in FIG. 10 attached to a dual chamber vial similar to that shown in FIG. 8 and forming a conduit between the vial and the IV bag, the arrows indicating a transfer of the contents of the vial into the IV bag.

FIG. 16 is a cross-sectional view of the spiked vial assembly of FIG. 15.

FIG. 17 is an enlarged view of the harpoon tip embedded within the piston of FIG. 16.

FIG. 18 is an enlarged view of the engaging edges of the case and vial of FIG. 16.

FIG. 19 is a cross-sectional view of the spiked vial assembly of FIG. 16 shown injecting the contents of the vial into an IV bag.

DESCRIPTION OF THE PREFERRED EMBODIMENT

Figure 4:
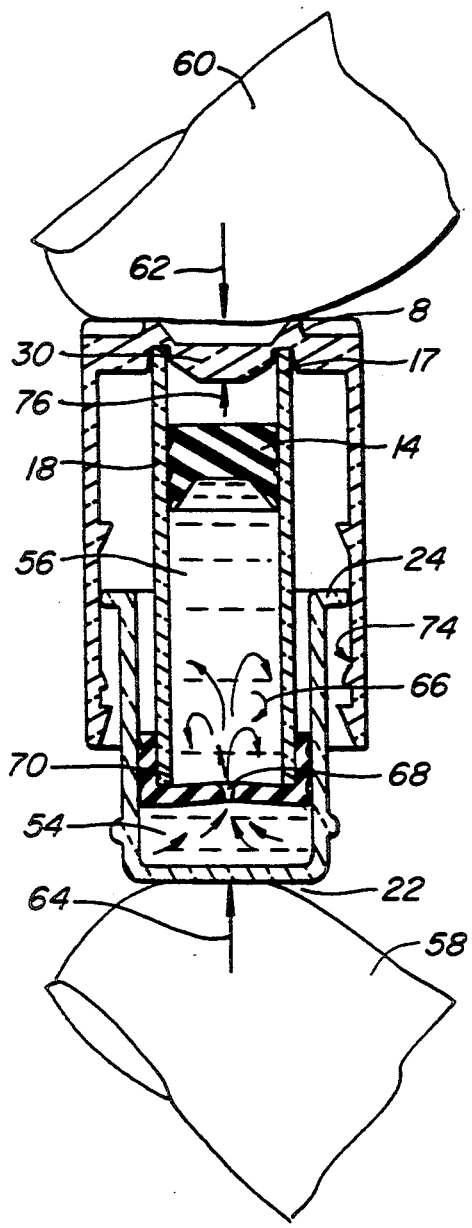
FIG. 4 shows the device in FIG. 3 being activated with the fluid pressure in the lower chamber tearing the diaphragm and causing turbulent mixing of the two components in the upper chamber with the piston travelling upwards as the upper chamber fills with both components.

Referring the reader to FIGS. 1 and 3, vial 2 includes a cylinder 18, piston 14, and a supplemental container or receptacle 22. Cylinder 18 and receptacle 22 are partially enclosed in housing 4. Housing 4, cylinder 18 and receptacle 22 are fabricated from transparent or translucent materials to allow the user to view the contents of vial 2. Cylinder 18 and receptacle 22 are preferably glass or a pharmaceutically compatible plastic; housing 4 is preferably made of polycarbonate.

Housing 4 is cylindrical in shape and has a pair of expansion slots 6 located 180° apart. Upper surface 8 of housing 4 has a plurality of gripping slots 10 to provide a non-slip surface for the user. A removable shield 30 is connected to housing 4 in a recessed housing aperture 28. Shield 30 is preferably a one-piece molded part with housing 4 and is connected to housing 4 by a continuous frangible connection 32. Alternatively, shield 30, as suggested in FIG. 13, could be friction fit or otherwise secured within the housing aperture 28. In either event, it is desired that shield 30 also keep the air space 55 above piston 14 sterile. Catch 40 is formed on the inner surface of housing 4. The function of catch 40 will be explained more fully below.

Referring now to FIG. 2, vial 2 is shown in an exploded view from the side showing the component parts. Housing 4 is open at its lower end 12. Cylinder 18 has a first end 17 and a second end 19. Piston 14 includes sealing ridges 16 sized to sealingly engage cylinder 18. Diaphragm 20 is made to be disposed about second end 19 of cylinder 18 and has sealing ridges 21 to create an air and liquid tight seal between outer surface of cylinder 18 and the inner surface of supplemental receptacle 22. Receptacle 22 is formed having a floor 26 and a rim 24. Rim 24 is formed to engage between a catch 36 and a protrusion 38 formed on housing 4 when in the premixed condition of FIGS. 1 and 3 or to engage with catch 40 on housing 4 when in the activated condition of FIG. 5.

Referring now to FIG. 3, showing vial 2 in the assembled and premixed condition, cylinder 18 is disposed between the upper surface 8 of housing 4 and receptacle 22. Housing 4 has a shoulder 34 and a seat 42 which is affixed to first end 17 of cylinder 18, such as by friction fit. Shield 30, frangibly connected to shoulder 34 at 23, covers the first end 17 of cylinder 18. Shield 30 is made of a rigid material which prohibits penetration by a needle cannula. As such, when shield 30 covers first end 17 of cylinder 18, a needle cannula cannot penetrate piston 14. Second end 19 of cylinder 18 is also precluded from penetration by a needle cannula in that it is enclosed by receptacle 22. Receptacle 22 is also made of a needle resistant material. In the preferred embodiment, housing 4 and receptacle 22 are transparent, but shield 30 is colored on it outer surface, preferably bright red, to indicate that access to cylinder 18 is restricted.

When piston 14 is disposed in cylinder 18 and diaphragm 20 is disposed on second end 19 of cylinder 18, an airtight and liquid-tight first chamber 56 is formed within cylinder 18. Diaphragm 20 seals between cylinder 18 and the inner surface of receptacle 22 such that when receptacle 22 is secured within housing 4 with rim 24 between catch 36 and protrusion 38, a second chamber 54 is formed between diaphragm 20 and floor 26 of receptacle 22. As shown in the cross section of FIG. 3, the result is a dual chamber vial 2 having a first chamber 56 housing a first component, and a second chamber 54 housing a second component when vial 2 is in the pre-mixed condition. Airspace 55 is formed between shield 30 and a flat surface 46 of piston 14.

In the embodiment shown in FIG. 3, diaphragm 20 is formed having a cavity 48 forming a thin, reduced-strength membrane 50. The dimensions of membrane 50 are such that diaphragm 20 can be ruptured or torn at membrane 50 by sufficient fluid pressure as will be more fully described below.

Referring now to FIG. 4, vial 2 is shown being activated as it is compressed from the premixed condition. As previously stated, vial 2 in the premixed condition shown in FIG. 3, isolates components in the first chamber 56 from the components contained in second chamber 54. Separation of the two components may be desirable for shipping and storage. When it is necessary to combine the two components, the user grasps vial 2 by placing a finger against upper surface 8 of housing 4 and a second finger or thumb 58 against the outer surface of floor 26 of receptacle 22. The user then squeezes his or her two fingers 60, 58 together as indicated by arrows 62, 64. The resultant compression forces pressurizes the component located in second chamber 54 as receptacle 22 slides up over housing 4.

Initially, vial 2 is taken out of the premixed condition as rim 24 slides up and over protrusion 38. As rim 24 slides over protrusion 38, housing 4 is allowed to expand because of expansion slots 6. In the preferred embodiment, second chamber 54 is initially filled with a liquid component. As receptacle 22 slides up into housing 4 towards first end 17 of cylinder 18, fluid pressure in second chamber 54 increases. The increase in fluid pressure causes thin membrane 50 of diaphragm 20 to rupture, thereby providing a channel 68 between second chamber 54 and first chamber 56.

The user continues to assert compression force 62, 64 forcing the fluid contents of second chamber 54 through channel 68 and into first chamber 56 where the contents of second chamber 54 and first chamber 56 turbulently mix as indicated by arrows 66. As the components mix in first chamber 56, the fluid volume of chamber 56 increases proportionally. The increase in volume in chamber 56 drives piston 14 up in cylinder 18 towards shield 30 as indicated by arrow 76. Air in air space 55 escapes between the rim at first end 17 of cylinder 18 and seat 42; a grooved air path or a one-way valve (to ensure sterility) may be provided if desired. Only when the contents of second chamber 54 are completely exhausted into first chamber 56 is piston 14 driven against shield 30 into a post-mixed condition illustrated in FIG. 5.

Figure 5:
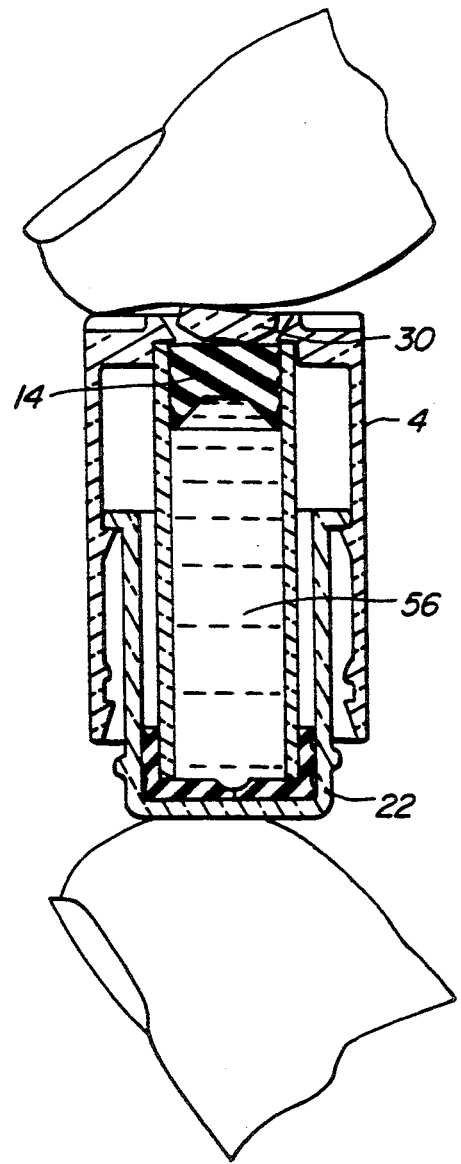
FIG. 5 shows the device illustrated in FIG. 4 in the fully activated position with the upper chamber filled with both mixed components and the shield dislodged from the safety position.

The post-mixed condition of vial 2, as shown in FIG. 5, is achieved when receptacle 22 is fully driven within housing 4 and the component parts of second chamber 54 and first chamber 56 have been turbulently mixed and combined within first chamber 56. When the increase in volume in first chamber 56 drives piston 14 into shield 30, shield 30 is dislodged from housing 4 by an audible snap. The audible snap is produced by breaking of the frangible connections between shield 30 and housing 4. Alternatively, when shield 30 is positioned within housing aperture 28 via a friction fit, as suggested in the embodiment of FIG. 13, audible pop as shield 30 is dislodged from its friction fit within housing aperture 28 may also be created. An aural indication is also created when rim 24 passes over catch 40. The user thus has an aural indication when shield 30 is dislodged from housing 4. This aural indicator, in conjunction with the freeing of shield 30, indicates to the user that the contents are fully mixed within the variable volume first chamber 56. Vial 2 is retained in the post-mixed condition by catch 40 retaining rim 24 of receptacle 22.

Figure 6:
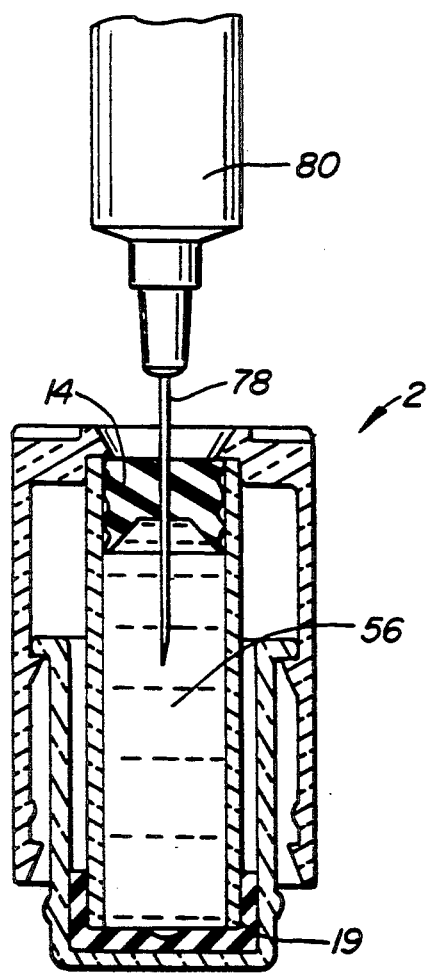
FIG. 6 shows the device of FIG. 5 with the shield removed and a needle cannula of a syringe penetrating the piston to withdraw the mixed pharmaceutical.

Once in the post-mixed condition, the shield 30 can be removed and a needle cannula 78 can be inserted through piston 14, which acts as a septum, as indicated in FIG. 6. Syringe 80 can now be used to draw out the contents of variable volume mixing region 51 located in vial 2. An important aspect of the invention is that as the contents of variable volume mixing region 51 is withdrawn from vial 2 through needle cannula 78, the fluid volume of variable volume region 56 decreases. As the volume decreases, the airtight and fluid-tight seals formed between piston 14 and cylinder 18, in combination with the seal formed by diaphragm 20 between receptacle 22 and cylinder 18, drives piston 14 down cylinder 18 towards second end 19 by hydraulic suction and prevents any ambient air from becoming entrained in variable volume region 56. This feature substantially prevents any inadvertent air bubbles from gathering within the pharmaceutical withdrawn from vial 2.

Figure 7:
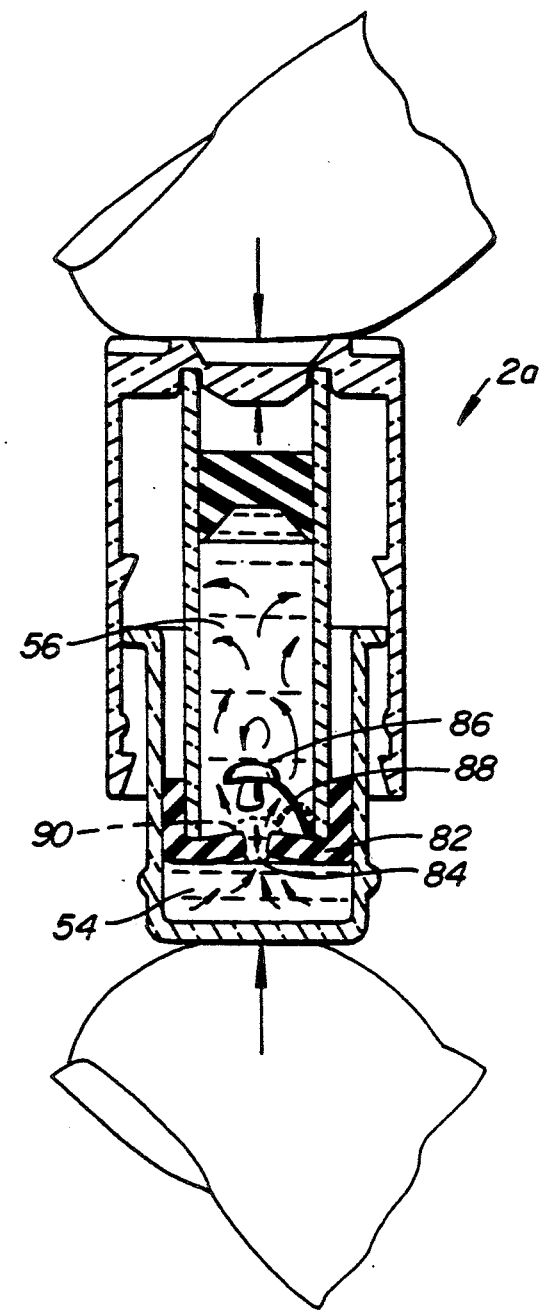
FIG. 7 shows a cross sectional view of an alternative embodiment of the invention having a diaphragm which includes a plug on a tether, the plug being dislodged from the diaphragm to open a channel allowing the two components to mix in the upper chamber.

An alternative embodiment of the invention is shown in FIG. 7. In the alternative embodiment, diaphragm 82 has an opening 84 which is sealed by plug 86 in the premixed condition. Plug 86 may be connected to diaphragm 82 using tether 88. Plug 86 may also be a separate component as well. When vial 2a is activated from the premixed condition to the post-mixed condition, the increase in fluid pressure in second chamber 54 causes plug 86 to dislodge from opening 84 allowing the components to mix in first chamber 56 as previously described. This embodiment has the added feature that plug 86 can be used to additionally mix the components combined in first chamber 56 when the user forcibly shakes vial 2 causing plug 86 to work as an agitator.

Figure 8:
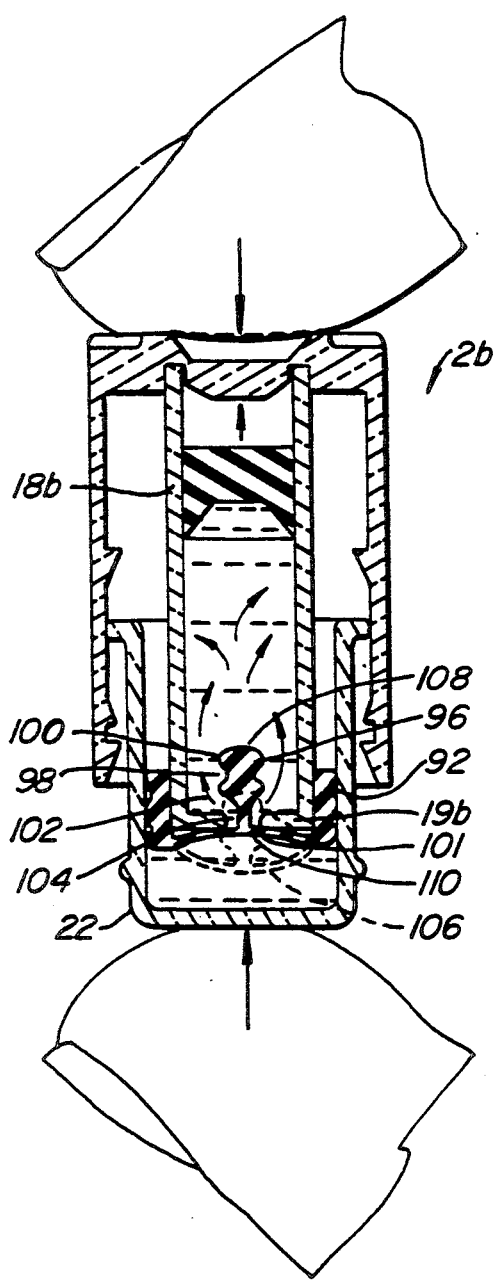
FIG. 8 is a cross-sectional view of another alternative embodiment of the invention having a gasket connected to a plug by a perforated diaphragm which, when inserted in an aperture of the cylinder, separates the two chambers.
Figure 9:
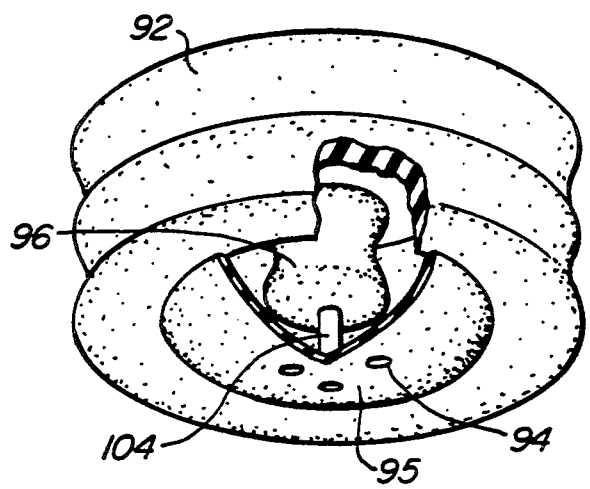
FIG. 9 is an engaged perspective, partial cross-sectional view of the gasket used in the embodiment illustrated in FIG. 8.

A second alternative embodiment of the invention is illustrated in FIGS. 8 and 9. In the second alternative embodiment of the invention, cylinder 18b is formed having second end 19b with a small aperture 101. Gasket 92 seals between cylinder 18b and receptacle 22. Gasket 92 is more fully depicted in FIG. 9. Gasket 92 is formed having a plurality of holes 94 formed through a membrane 95 to which a stem 104 of plug 96 extends. Plug 96 is positionable in aperture 101 to seal and isolate first chamber 56 and second chamber 54 in the premixed position. When vial 2b is moved from the premixed position, fluid pressure in second chamber 54 causes plug 96 to be dislodged from aperture 101 forming a channel 110 between first chamber 56 and second chamber 54.

When vial 2 contains a pharmaceutical which needs to be administered into a conventional IV bag, a spike adapter 120 can be used to form a conduit between vial 2 and the IV bag. Referring now to FIG. 10, spike adapter 120 includes a body portion 122 having a first end 124 and a second 126. First end 124 and second end 126 are both open and have a piercing tip 128, 130 respectively. First end 124 is covered by a removable cap 132, and second end 126 is removably covered by cap 134.

FIG. 11 illustrates spike adapter 120 in cross section with cap 132 and cap 134 disposed over first end 124 and second end 126, respectively. Body portion 122 is formed having a cannula 136 along its longitudinal axis connecting tip 128 and tip 130. Body 122 also includes a shoulder 142.

Referring now to FIGS. 12 and 13, cap 134 is removed and second end 126 is inserted into a spike port 144 of a conventional IV bag 146. Tip 128 of first end 124 is then passed through the piston 14 of a vial 2c after vial 2c is placed in the post-mixed condition. The contents of variable volume region 51 of vial 2c is driven from vial 2c, through cannula 136 and into IV bag 146 by forcing piston 14 into cylinder 18 through the application of force to floor 26c of receptacle 22c and shoulder 142 of spike adapter 120 as indicated by arrows 148, 150.

Figure 14:
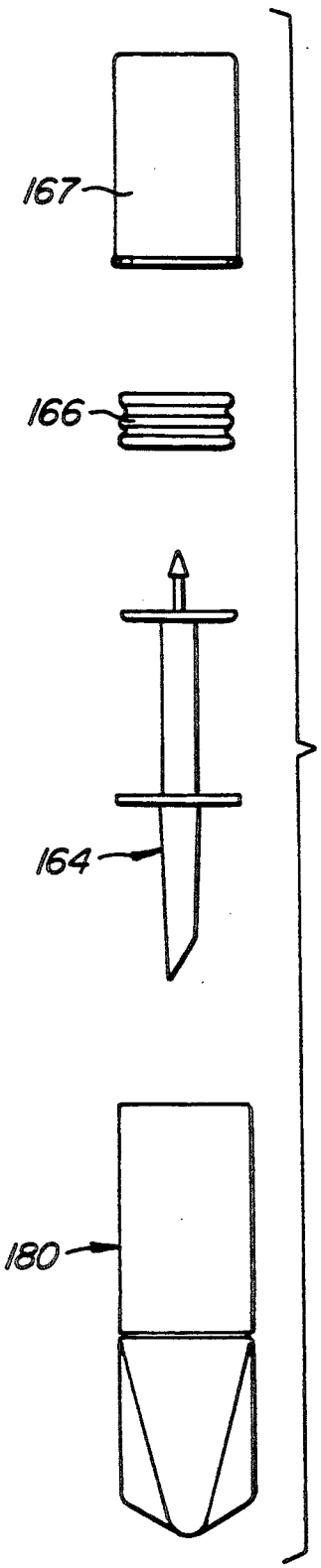
FIG. 14 is an exploded side view of a spiked vial assembly.
Figure 15:
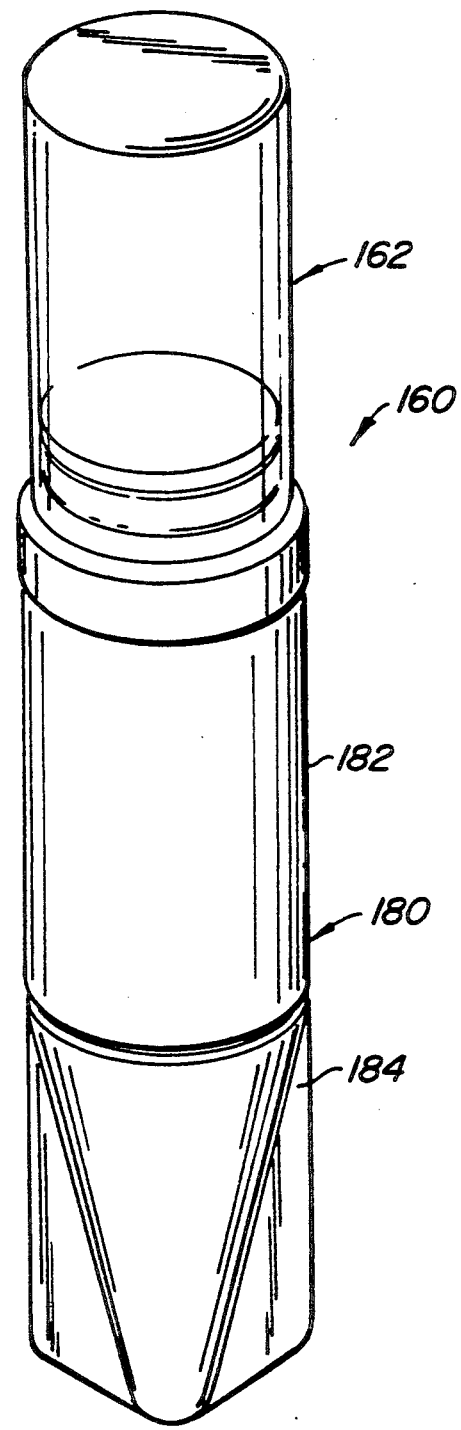
FIG. 15 is a perspective view of the spiked vial assembly of FIG. 14 in an assembled condition.

Turning now to FIGS. 14–16, a spiked vial assembly 160 is shown and includes a vial 162 and a spike adaptor 164. Vial 162 includes a piston 166 which moves within the barrel to create a variable volume region 168 within vial 162. Spike adaptor 164 includes a harpoon tip 170, see FIG. 17, positioned within a complementary open region 172 formed within piston 166 when in the premixed condition of FIG. 16. Spike adaptor 164 also includes a primary shoulder 174 positioned towards a spike tip 178, and a secondary shoulder 176, positioned near harpoon tip 170.

Spiked vial assembly 160 also includes a case 180 including a first, guide portion 182 and a second, protective portion 184 frangibly connected to first portion 182 at a frangible connection 186. The outer periphery of primary shoulder 174 is secured to first portion 182 adjacent frangible connection 186, such as by using an adhesive or ultrasonic welding techniques. The other end 188 of first portion 182, as seen best in FIG. 18, slidably engages the outer surface 190 of vial 162. Vial 162 has a bead 192 at its open end which engages a detent region 194 of outer end 188. This helps to prevent the inadvertent movement of spike adaptor 164 and case 180 therewith towards vial 162. When it is desired to inject the contents of vial 162 into an IV bag 146, second portion 184 of case 180 is removed from first portion 182 by breaking frangible connection 186. Spike tip 178 is then inserted into spike port 144 as shown in FIG. 19. The user then forces vial 162 against spike adaptor 164 as indicated by arrows 148, 150 which causes harpoon tip 170 to move from region 172, as shown in FIG. 17, to region 196, as shown in FIG. 19. This forces harpoon tip 170 through the piston surface 198 so that cannula 136 fluidly connects the interior of IV bag 146 with variable volume region 168 of vial 162. Continued movement in the direction of arrows 148, 150 causes piston 166 to move within variable volume region 168 forcing the contents of variable volume region 168 through cannula 136 and into IV bag as shown in FIG. 19.

Spiked vial assembly 160 could be constructed with a plain piercing tip positioned opposite piston 166 when in the premixed condition of FIG. 16. However, the tactile indication of the movement of harpoon tip 170 from region 172 to region 196 would be lost. Also, the sanitary advantages accruing from housing harpoon tip 170 within piston 166 would be lost as well.

Other modifications and variations can be made to the disclosed embodiments without departing from the subject of the invention as defined in the following claims. For example, although the contents of the second chamber will generally always be a liquid, the contents of the first chamber, before mixing, can be a liquid or a solid. The opening at second end 19 of cylinder 18 could be through the sidewall of the cylinder. Housing 4 is quite useful but optional. If housing 4 is not used, removable shield 130 can be mounted directly within the interior of cylinder 18 adjacent first end 17. This would, however, typically require some provision to permit air with an air space 55 to escape when moving from the premixed condition of FIG. 3 to the postmixed condition of FIG. 5 while maintaining the interior of cylinder 18 sterile. This could be accomplished, for example, through the use of a one-way valve.

What is claimed is:

1. A component mixing vial, for use with first and second components, the second component being a liquid component, comprising:

a mixing container having first and second ends, openings at the first and second ends and a hollow elongate portion communicating with the first end and extending towards the second end;

a piston positioned within the elongate portion of the mixing container forming an airtight barrier across the elongate portion and movable from a pre-mix position, away from the first end, to a post-mix position, towards the first end;

a seal covering the second open end of the mixing container, the seal including a diaphragm with a pressure sensitive weakened region, the first component being within a variable volume mixing region between the seal and the piston;

a supplemental container, coupled to the second end of the mixing container, the supplemental container containing the second component;

means for forcing the second component past the seal into the variable volume mixing region causing the first and second components to mix in the variable volume mixing region and forcing the piston towards the first end to the post-mix position;

means for preventing needle access to the piston while the piston is in the pr-mix position and for permitting needle access to the piston when the piston is in the post-mix position, the piston being pierceable by a hollow needle at the post-mix position to permit the mixed contents within the variable volume region to be withdrawn through the hollow needle; and a hollow spike adaptor including a spike end, adapted to engage with a spike post of an IV bag, and a hollow needle end, adapted to pierce the piston when at the post-mix position so to permit the contents of the variable volume mixing region to be transferred to the IV bag through the spike adaptor.

2. The vial of claim 1 further comprising removable means for covering the spike end prior to use, the removable means frangibly coupled to the first shoulder.

3. The vial of claim 1 wherein the hollow needle end is generally arrowhead-shaped, the piston is an elastomeric piston and the hollow needle end is imbedded within the piston.

4. The vial of claim 3 wherein the piston includes first and second complementarily shaped open regions for housing the arrowhead-shaped hollow needle end, the hollow needle end movable between the first and second complementarily shaped open regions.

5. A spiked vial assembly, for injecting a liquid through the spike port of an IV bag, comprising:
- a cylinder having an open end, a circumferential sidewall and a bead extending outwardly from the circumferential sidewall near the open end;
- a piston mounted within the cylinder to define a variable volume region within the cylinder for containing the liquid;
- a hollow spike adaptor having a spike tip and a needle tip coupled by a cannula, a first shoulder positioned near the spike tip and extending outwardly from an outside surface of the cannula, a second shoulder positioned near the needle tip and extending outwardly from the outside surface of the cannula;
- means for driving the needle tip from an inactive position, through the piston and into the variable volume region to an active position to permit the liquid to be driven from the cylinder through the spike adaptor and into the IV bag by driving the piston through the cylinder; and
- means for guiding the spike adaptor as the spike adaptor moves from the inactive position to the active position and then as the piston is driven through the cylinder, the guiding means including a first portion coupled to the first shoulder, the first portion including a detent region configured to releasably engage the bead and slidably engage the circumferential sidewall of the cylinder.

6. The assembly of claim 5 wherein the needle tip is generally arrowhead-shaped, the piston is an elastomeric piston and the needle-tip imbedded within the piston.

7. The assembly of claim 6 wherein the piston includes first and second complementarily shaped open regions for housing the arrowhead-shaped needle tip, the needle tip movable between the first and second complementarily shaped open regions.

8. The assembly of claim 5 further comprising removable means for covering the spike prior to use, the removable means frangibly coupled to the first shoulder.

* * * * *